United States Patent [19]

Lopez et al.

[11] 4,211,773
[45] Jul. 8, 1980

[54] 5-SUBSTITUTED 1-(2'-DEOXY-2'-SUBSTITUTED-β-D-ARABINOFURANOSYL)PYRIMIDINE NUCLEOSIDES

[75] Inventors: Carlos Lopez, New York; Kyoichi A. Watanabe, Portchester; Uri Reichman; Jack J. Fox, both of White Plains, all of N.Y.

[73] Assignee: Sloan Kettering Institute for Cancer Research, New York, N.Y.

[21] Appl. No.: 948,189

[22] Filed: Oct. 2, 1978

[51] Int. Cl.$^2$ .................. A61K 31/70; C07H 17/00
[52] U.S. Cl. ................................. 424/180; 536/23
[58] Field of Search ....................... 536/23; 424/180

[56] References Cited

U.S. PATENT DOCUMENTS

| 3,155,646 | 11/1964 | Hunter | 536/23 |
| 3,282,921 | 11/1966 | Verheyden et al. | 536/23 |
| 3,539,550 | 11/1970 | Greenberg et al. | 536/23 |
| 3,687,931 | 8/1972 | Verheyden et al. | 536/23 |
| 3,721,664 | 3/1973 | Hoffer | 536/23 |
| 3,817,982 | 6/1974 | Verheyden et al. | 536/23 |
| 3,870,700 | 3/1975 | Kotick et al. | 536/23 |
| 3,873,516 | 3/1975 | Kotick et al. | 536/23 |

OTHER PUBLICATIONS

Reichman, U., et al., Carbohydrate Research, 42 (1975), 233–240.
Ritzmann, G., et al., Carbohydrate Research, 39 (1975), 227–236.
Wright, J., et al., J. Medic. Chem., 13, 269 (1970).

Primary Examiner—Johnnie R. Brown
Assistant Examiner—Blondel Hazel
Attorney, Agent, or Firm—Sprung, Felfe, Horn, Lynch & Kramer

[57] ABSTRACT

Pyrimidine nucleosides exhibiting anti-viral and anti-tumor effects have the formula

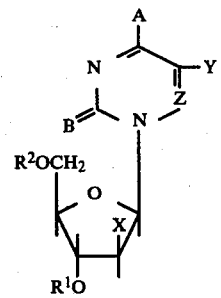

wherein
A is $OR^3$, $SR^3$, $NR^3R^4$ or NHacyl wherein $R^3$ and $R^4$ are the same or different and are hydrogen, lower alkyl of 1 to 7 carbon atoms, aralkyl, or aryl;
NHacyl is alkanoyl or aroyl amide;
B is oxygen or sulfur;
X is halogen, alkylsulfonyl or arylsulfonyl;
Y is halogen, amino, monoalkyl- or monoaralkylamino, dialkylamino, aminomethyl, hydroxymethyl, lower alkyl, aryl, aralkyl, vinyl and substituted vinyl or ethynyl and substituted ethynyl;
Z is methyne or nitrogen;
$R^1$ and $R^2$ are the same or different and are hydrogen acyl or aroyl.

10 Claims, No Drawings

5-SUBSTITUTED 1-(2'-DEOXY-2'-SUBSTITUTED-β-D-ARABINOFURANOSYL)PYRIMIDINE NUCLEOSIDES

The invention described herein was made in the course of work under a grant or award from the Department of Health, Education and Welfare.

BACKGROUND

This invention relates to novel 5-substituted 1-(2'-deoxy-2'-substituted-β-D-arabinofuranosyl)pyrimidine nucleosides which are useful as anti-viral and anti-cancer agents.

5-Bromo- and/or 5-iodo-2'-deoxycytidine inhibit the replication of herpes simplex virus (HSV) (Schildkraut et al, Mol. Pharmacol., 11, 153 (1975); Greer et al, Ann. N.Y. Acad. Sci., 255, 359 (1975)) as effectively as their corresponding deoxyuridine analogs. The deoxycytidine analogs are less toxic to uninfected cells than are 5-iodo (or 5-bromo)-2'-deoxyuridine apparently as a result of a virus-induced pyrimidine nucleoside kinase which converts the 5-halogenated deoxycytidines to the 5-halogenated deoxycytidylates and thence to the corresponding deoxyuridylates.

1-β-D-Arabinofuranosylcytosine (ara-C), is a known anti-cancer agent (Talley et al, Cancer, 20, 809 (1967)) and also inhibits the multiplication of several DNA virus in cell culture (Buthala, Proc. Soc. Exptl. Biol. Med., 115, 69 (1964); Feldman, et al, ibid., 122, 243 (1966)). Therapeutic trials of ara-C in herpes infections were not encouraging because its therapeutic to toxic ratio approached unity (Lauter et al, Antimicrobial Agents Chemother., 6, 598 (1974)). Although 1-β-D-arabinofuranosyluracil (ara-U) is devoid of anti-viral or anti-cancer activity, the 5-halogeno analogs show anti-viral activity (Underwood et al, Arch. Ophthamol., 72, 505 (1964)). Ara-T is active against HSV types 1 and 2 as well as against equine herpesvirus (Gentry et al, Virology, 65, 294 (1975); Aswell et al, Proc. Amer. Soc. Microbiol., 240 (1975)). 5-Methyl-ara-C is also active against herpesvirus infected cells in which deoxycytidine deaminase is present indicating that this nucleoside serves as an intracellular donor of ara-T that is phosphorylated to the nucleotide which then inhibits viral replication (Aswell et al, Ann. N.Y. Acad. Sci., 284, 342 (1977)). 5-Methyl-ara-C is devoid of anti-cancer activity. (Doerr et al, J. Med. Chem., 10, 247 (1967)). The 5-halogeno-ara-C derivatives have also shown anti-herpesvirus activity and are active against experimental herpes keratitis in rabbits (Renis et al, Antimicrobial Agents Chemotherap., 675 (1967)).

SUMMARY

Nucleosides of the invention can be represented by Formula I as follows:

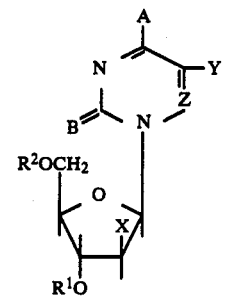

wherein
A is $OR^3$ (keto or enol), $SR^3$, $NR^3R^4$ or NHacyl;
$R^3$ and $R^4$ are the same or different and are hydrogen, lower alkyl of 1 to 7 carbon atoms such as methyl, ethyl, propyl and the like, aralkyl such as benzyl, benzhydryl, p-methoxybenzyl and the like, or aryl such as phenyl, p-chlorophenyl, tolnyl, p-methoxyphenyl, naphthyl and the like.
NHacyl may be an alkanoyl or aroyl amide. The term "alkanoyl" is meant to include an alkyl carbonyl radical wherein alkyl is a straight or branched chain saturated or unsaturated hydrocarbon radical having from 1 to 20 carbon atoms.
B is oxygen or sulfur;
X is halogen such as fluorine, chlorine, bromine or iodine as well as pseudohalogen such as lower alkylsulfonyl group of 1 to 5 carbons such as methyl-, ethyl-, propyl-, isopropyl-, butyl-, isobutyl-, tert-butyl- and pentylsulfonyl or arylsulfonyl such as benzene-, p-toluene-, p-nitrobenzenesulfonyl grouping.
Y is halogen such as fluorine, chlorine, bromine or iodine; amino; monoalkyl- or monoaralkylamino such as methylamino, ethylamino, propylamino or benzylamino and the like; dialkylamino such as dimethylamino, diethylamino, dibenzylamino, pyrrolidino, piperidino or molpholino and the like; aminomethyl; hydroxymethyl; lower alkyl of 1 to 7 carbon atoms such as methyl, ethyl, propyl, isopropyl, butyl, isobutyl, tert-butyl, pentyl and the like; aryl such as phenyl, p-tolyl, p-chlorophenyl, p-aminophenyl, p-nitrophenyl, p-anisyl and the like; aralkyl such as benzyl, benzhydryl, p-chlorobenzyl, m-chlorobenzyl, p-nitrobenzyl and the like; vinyl and substituted vinyl; ethynyl and substituted ethynyl. Substituted vinyl or substituted ethynyl designates substitution of the β position of vinyl or ethynyl by alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like.
Z is methyne (—CH=) or nitrogen;
$R^1$ and $R^2$ are the same or different hydrogen or acyl groups which may be alkanoyl groups of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like. $R^1$ and $R^2$ can also by aroyl such as benzoyl and naphthoyl wherein the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl and the like. $R^2$ may also be adamantoyl.

DESCRIPTION

The preferred starting materials for the process of the present invention can be subsumed under general Formula II as follows:

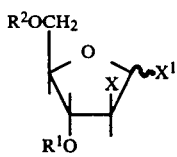

$R^1$ and $R^2$ are as defined previously.

X is halogen such as fluorine, chlorine, bromine and iodine as well as pseudohalogens such as lower alkylsulfonyl group of 1 to 5 carbons such as methyl-, ethyl-, propyl-, isopropyl-, butyl-, isobutyl-, tert-butyl- and pentylsulfonyl or arylsulfonyl such as benzene-, p-toluene-, p-nitrobenzenesulfonyl grouping.

$X^1$ is chlorine or bromine.

The synthesis of Formula II compounds is known (Reichman et al. Carbohydr. Res., 42, 233 (1975); Ritzman et al, ibid., 39, 227 (1975)).

The starting materials of Formula II are reacted with a nucleophile of general Formula III:

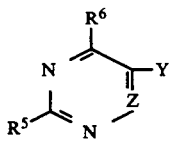

$R^5$ is a tri-substituted-silyloxy or tri-substituted-silylmercapto group. The tri-substituted silyl may be trimethyl-, triethyl-, tripropyl-, tri-isopropyl-, tributyl-, tert-butyldimethyl-, tetramethyleneisopropyl-, tetramethylene-tert-butyl-, tribenzyl-, or phenyldimenthylsilyl or the like.

$R^6$ is dialkylamino, alkylmercapto, alkoxy, tri-substituted-silyloxy bis(tri-substituted silyl)amino, tri-substituted-silylmonoalkylamino, tri-substituted-silylalkanoylamino, tri-substituted-silylaroylamino or tri-substituted silylmercapto and the like. The tri-substituted-silyl is the same as in $R^5$ above. The designation of silylalkanoylamino may be silylacetamido, silylpropionamide, and the like, and silylaroylamino may be silylbenzamido, silyltoluamido, silylanisamido and the like. The dialkylamino may be dimethylamino, diethylamino, dibenzylamino, pyrrolidino, piperidino, morpholino. Alkylamino may be methylamino, ethylamino, propylamino and benzylamino. Alkymercapto and alkoxy designate a sulfur or oxygen substituted by a lower alkyl group of 1 to 7 carbon atoms such as methyl, ethyl, propyl and the like.

Z is methyne (—CH=) or nitrogen.

Y is halogen (fluorine, chlorine, bromine or iodine); lower alkyl of 1 to 5 carbon atoms such as methyl, ethyl, propyl, butyl, isobutyl, tert-butyl, pentyl and the like; aryl such as phenyl, p-tolyl, p-chlorophenyl, p-aminophenyl, p-nitrophenyl, p-anisyl and the like; aralkyl such as benzyl, benzhydryl, p-chlorobenzyl, m-chlorobenzyl, p-nitrobenzyl and the like; vinyl and substituted vinyl; ethynyl and substituted ethylnyl; bis(tri-substituted-silyl)amino; tri-substituted-silylalkylamino; bis(tri-substituted-silyl)aminomethyl; and tri-substituted-silyloxymethyl groups. The designation of tri-substituted-silyl is the same as described previously. Substituted vinyl or substituted ethynyl designates substitution of the β-position of vinyl or ethynyl by alkyl, aralkyl or aryl. Alkyl designates saturated hydrocarbon of 1 to 5 carbon atoms such as methyl, ethyl, propyl, butyl, pentyl and the like; aralkyl such as benzyl, p-nitrobenzyl, p-chlorobenzyl and the like; aryl such as phenyl, p-nitrophenyl, p-chlorophenyl, tolyl, anisyl, naphthyl and the like.

With respect to the above definitions, groups such as alkyl, etc. can have the following carbon atom contents:

| GROUP | CARBON ATOM CONTENT | |
|---|---|---|
| | GENERAL | PREFERRED |
| Alkyl | 1–20 | 1–7 |
| Aryl | 6–18 | 6–10 |
| Vinyl | 2 to 8 | 2–4 |
| Acetenyl | 2 to 8 | 2–4 |
| Carboxylic Acid | | |
| Aliphatic | 1 to 20 | 2, 6–20 |
| Aromatic | 7 to 11 | 7–9 |

The reaction is carried out in an aprotic solvent such as halogenated hydrocarbon (e.g., methylene chloride, chloroform, 1,2-dichloroethane, etc.), aromatic hydrocarbon (benzene, toluene, xylene, etc.), carboxylic acid derivatives such as ethyl acetate, acetonitrile or N,N-dimethylacetamide, preferably in methylene chloride or dichloroethane at temperature in the range of from 0° to 140° C. preferably from 20° to 30° C. in a period of from 6 hours to 10 days.

The molar ratio of the reactants, Formula II to Formula III, can be 1 to 10, preferably 1 to 3.

Upon completion of the reaction, the reaction mixture is quenched, suitably by adding excess alkanol such as methanol, ethanol, propanol and the like to the reaction mixture to hydrolyze the tri-substituted-silyl groups. Insoluble material is removed by filtration and washed with solvent such as methylene chloride. The combined filtrate and washings are evaporated to dryness in vacuo.

3',5'-Di-O-acyl nucleosides (Formula I above) can be obtained in pure condition either by direct crystallization of the residue from various solvents such as alkanol preferably ethanol or solvent systems such as alkanol-dialkyl ether or petroleum ether, preferably ethanol-diethyl ether, or by chromatography over a column of silica gel G60 using various solvent systems preferably chloroform-methanol (40:1 v/v) as the eluent.

The free Formula I nucleoside wherein X is F and $R^1$ and $R^2$ are hydrogen is obtained by either saponification of the 3',5'-di-O-acyl intermediate with alkali metal alkoxide in alkanol preferably 0.01 to 0.1 M sodium methoxide in methanol or when A is not SH or SR by treatment of the 3',5'-protected nucleoside with amine-alkanol mixture preferably 10 to 30% methanolic ammonia at temperature between −10° and 100° C. preferably 10° to 30° C. for 5 minutes to 3 days.

The free Formula I nucleoside wherein X is Cl or Br and $R^1$ and $R^2$ are hydrogen, is prepared from the corresponding 3',5'-di-O-alkanoyl intermediate (Formula I wherein X is Cl or Br and $R^1$ and $R^2$ are same or different lower alkanoyl groups such as acetyl, propionyl, butyryl and the like) by treatment with mineral acid in water or alkanol, preferably 5 to 15% hydrogen chloride in methanol.

The free nucleoside (Formula I wherein A is an amino, monosubstituted amino, or disubstituted amino group) forms acid addition salts with both organic and inorganic acids. Preferable acid addition salts are the pharmaceutically-acceptable acid addition salts. Non-pharmaceutically acceptable acid addition salts can be converted to the pharmaceutically acceptable acid addition salts by ion-exchange techniques well known in the art. Examples of pharmaceutically acceptable acid addition salts include hydrochloric acid, hydrobromic acid, sulfuric acid, phosphoric acid, citric acid, acetic acid, succinic acid, maleic acid, methanesulfonic acid, p-toluenesulfonic acid and the like.

The free nucleosides (Formula I) and their acid addition salts are useful therapeutic agents exhibiting anti-viral and anti-cancer activity and may be employed in the form of pharmaceutical preparations which contain them in association with a compatible pharmaceutical carrier which can be an organic or inorganic inert carrier material suitable for enteral or parenteral administration such as, for example, water, gelatin, gum arabic, lactose, starches, magnesium stearate, talc, vegetable oils, polyalkylene glycols, petroleum jelly, etc. The pharmaceutical preparations can be made up in solid form (e.g., as tablets, dragees, suppositories or capsules) or in liquid form (e.g., as solutions, suspensions or emulsions). The preparations may be sterilized and/or may contain adjuvants such as preserving, stabilizing, wetting or emulsifying agents, salts for varying the osmotic pressure or buffers. Such preparations may also contain other therapeutic agents.

Formula I 4-thiopyrimidine nucleosides wherein A is SH are obtained by thiation of a Formula I 3',5'-di-O-acyl nucleoside wherein A is OH and Y is fluorine, alkyl, aryl, aralkyl, vinyl or ethynyl, with phosphorus pentasulfide ($P_2S_5$) in dioxan at the temperature range of 20° to 120° preferably 25° to 100° for a period of 10 minutes to 24 hours. The molar ratio with respect to $P_2S_5$ is from 1:0.5 to 1:2. The free 4-thiopyrimidine nucleoside is obtained by saponification as described previously.

4-Alkylmercapto- or 4-aralkylmercaptopyrimidine nucleoside wherein A is SR is obtained by treatment of the free 4-thiopyrimidine nucleoside (Formula I, A=SH, $R^1=R^2=H$) with alkyl or aralkyl halide or dialkyl sulfate in water or alkanol in the presence of alkali metal hydroxide or alkali metal alkoxide, preferably 1.0 to 1.2 equivalents of sodium hydroxide in water or 1.0 to 1.2 equivalents of sodium methoxide in methanol. Alkyl halide designates bromide or iodide of lower alkyl of 1 to 5 carbon atoms such as methyl, ethyl, propyl, isopropyl, butyl, isobutyl, tert-butyl, pentyl and the like. Aralkyl halide includes chloride or bromide of benzyl, p-chlorobenzyl, p-bromobenzyl, p-nitrobenzyl, p-methylbenzyl, p-methoxybenzyl and the like.

4-Amino-substituted nucleosides (Formula I, $R^1$, $R^2=H$, $A=NR^3R^4$ wherein $R^3$ and $R^4$ may be the same or different groups such as H, alkyl, aralkyl or aryl as defined above; Y and Z are as defined in Formula III above; B=sulfur or oxygen), are also obtained from 4-thio nucleosides (Formula I, A=SH; $R^1$, $R^2=H$), 4-alkyl- or aralkylmercapto nucleosides (Formula I, A=SR; $R^1$, $R^2=H$) or their 3',5'-di-O-acyl analogs (Formula I, A=SH or SR wherein $R^1$ and $R^2$ are the same or different alkanoyl or aroyl groups) by treatment with the corresponding amine (including ammonis) in water or alkanol (preferably methanol) at a temperature range of 0°–150°, under a pressure range of from 1 to 5 atms.

4-Hydroxy-substituted nucleosides (Formula I wherein A is ON) are also prepared by acid hydrolysis of 4-amino or 4-acylamino-nucleosides (Formula I, $A=NR^3R^4$ or NHacyl) and 4-thio or 4-substituted-thio nucleosides (Formula I, A=SH or SR). Thus treatment of 4-amino or 4-acylamino nucleosides (Formula I, $A=NR^3R^4$ or NHacyl; Y=F, Cl, Br, etc.; as defined in Formula III; Z=CH or N, B=O or S, X as defined in Formula II; $R^1$ and $R^2=H$ or as defined in Formula II with aqueous mineral or organic acid, preferably 50–80% acetic acid, at reflux for 10 minutes to 24 hours followed by evaporation of the solvent in vacuo affords the corresponding 4-hydroxy nucleosides. Also treatment of 4-thio or 4-substituted-thio nucleosides (Formula I, A=SH or SR as defined above; $R^1$, $R^2$, B, X, Y, Z as defined above for the 4-amino analogs) with aqueous mineral or organic acid, preferably 1.5 to 6 equivalents of monochloroacetic acid under reflux for 1 to 72 hours followed by removal of the solvent in vacuo affords the corresponding 4-hydroxy nucleosides.

5-Halogeno nucleosides (Formula I, A=OH, Y=Cl, Br or I) are also obtained by direct halogenation. 5-Chloropyrimidine nucleosides (Formula I, A=OH, Y=Cl) are prepared by treatment of the 5-unsubstituted derivatives (Formula I, A=OH, Y=H) in water, alkanol of 1 to 4 carbon atoms such as methanol, ethanol, propanol or butanol and the like, or lower alkanoic acid of 2 to 6 carbon atoms such as acetic, propionic, butyric, valeric or caproic acid and the like, or dioxan or a mixture of water and dioxan, most preferably acetic acid, with 1.5 to 2 equivalents of chlorine, preferably in carbon tetrachloride solution, under reflux for 10 to 20 minutes followed by evaporation to dryness in vacuo. Bromination and iodination are also carried out similarly at temperature range of 15° to 60° by replacing chlorine by bromine or iodine. The most preferable solvent for these reactions is dioxan and the presence of a catalytic amount of nitric acid is required. N-Bromosuccinimide and N-iodosuccinimide are also effective halogenating agents.

The cytosine analogs (Formula I, $A=NH_2$, $NR^3R^4$) are also brominated or iodinated similarly using bromic or iodic acid as catalyst. Again, N-bromosuccinimide, N-iodosuccinimide or iodine chloride are effective halogenating agents.

5'-O-Alkanoyl nucleosides (Formula I, $R^2$=alkanoyl group of 4 to 20 carbon atoms; $R^1$=H; A, B, X, Y and Z are as defined in Formula I) are obtained by treatment of the corresponding free nucleoside or the HCl salt (if the nucleoside contains amino group) with 1.1 equivalents of alkanoyl halide in dimethyl formamide or dimethyl acetamide at a temperature range of 0°–100° preferably at room temperature for a period of 1 to 72 hours. Alkanoyl halide includes chloride or bromide of saturated or unsaturated fatty acid containing 4 to 20 carbon atoms such as n-butyric, isobutyric, n-valeric, isovaleric, caproic, capric, lauric, myristic, palmitic, stearic, arachidic, stilligic, palmitoleic, oleic, linolenic or arachidonic acid and the like.

After completion of the reaction, the mixture is concentrated in vacuo, and the residue is thoroughly triturated first with ether, preferably diethyl ether, and then by 1-2 N sodium bicarbonate solution. The residue is crystallized from an appropriate alkanol such as methanol, ethanol, propanol, isopropanol, n-butanol and the like or from an alkanoic acid ester such as ethyl acetate, methyl propionate and the like or a mixture of such solvents.

5'-O-Aroyl nucleosides (Formula I, $R^2$=aroyl such as benzoyl, toluoyl, p-chloro-benzoyl, p-nitrobenzoyl, anisoyl, naphtoyl, and the like; $R^1$=H; A, B, X, Y and Z are as defined for Formula I) and 5'-O-adamantoyl nucleosides (Formula I, $R^2$=adamantoyl); $R^1$=H; A, B, X, Y and Z are as defined for Formula I) are also prepared by a similar manner from the corresponding free nucleosides or the HCl salt (if the nucleoside contains amino group) by treatment with 1.5 to 4 equivalents of the corresponding acid halides.

The following examples are intended to further illustrate the inventions without limiting same.

EXAMPLE 1

To a solution of 3-O-acetyl-5-O-benzoyl-2-deoxy-2-fluoro-D-arabinofuranosyl bromide (3.6 g, 0.01 mol) in methylene chloride (50 ml) is added a methylene chloride solution of 5-chloro-tris(trimethylsilyl)cytosine [prepared from 4.3 g, 0.03 mol. of 5-chlorocytosine as follows: a mixture of 5-chlorocytosine and 5–15 mg of ammonium sulfate in 43 ml of hexamethyldisilazane is heated to reflux until a clear solution is obtained. The excess hexamethyldisilazane is removed by evaporation in vacuo and the residue is dissolved in 25 ml of methylene chloride]. The mixture is stirred for 5 days at room temperature. Methanol (7 ml) is added to the reaction mixture, and the suspension is filtered through a Celite pad which is thoroughly washed with methylene chloride. The combined filtrate and washings are evaporated to dryness in vacuo and the residue is crystallized from ethanol to give 860 mg of 1-(3-O-acetyl-5-O-benzoyl-2-deoxy-2-fluoro-β-D-arabinofuranosyl)-5-chlorocytosine, m.p. 233°.

Microanalysis ($C_{18}H_{17}ClFN_3O_6$). Calcd. C, 50.77; H, 4.02; F, 4.46; N, 9.87. Found: C, 51.02; H, 4.18; F, 4.34; N, 9.80.

The mother liquor of crystallization is evaporated to dryness in vacuo to a syrup which is chromatographed on a column of silica gel G60 (~100 g) using chloroform-methanol (40:1 v/v) as the eluent. Twenty ml fractions are collected and each fraction is checked by tlc. Appropriate fractions (7–20) are collected and evaporated to dryness in vacuo, and the residue is crystallized from ethanol to give an additional product (968 mg) identical in all respects with an authentic sample.

By following the same procedure but using the corresponding cytosine analogs as starting materials, the following compounds are also prepared:

1-(3-O-acetyl-5-O-benzoyl-2-deoxy-2-fluoro-β-D-arabinofuranosyl)-5-bromocytosine.

1-(3-O-acetyl-5-O-benzoyl-2-deoxy-2-fluoro-β-D-arabinofuranosyl)-5-iodocytosine.

1-(3-O-acetyl-5-O-benzoyl-2-deoxy-2-fluoro-β-D-arabinofuranosyl)-5-methylcytosine.

1-(3-O-acetyl-5-O-benzoyl-2-deoxy-2-fluoro-β-D-arabinofuranosyl)-5-ethylcytosine.

1-(3-O-acetyl-5-O-benzoyl-2-deoxy-2-fluoro-β-D-arabinofuranosyl)-5-benzylcytosine.

1-(3-O-acetyl-5-O-benzoyl-2-deoxy-2-fluoro-β-D-arabinofuranosyl)-5-phenylcytosine.

1-(3-O-acetyl-5-O-benzoyl-2-deoxy-2-fluoro-β-D-arabinofuranosyl)-5-vinylcytosine.

1-(3-O-acetyl-5-O-benzoyl-2-deoxy-2-fluoro-β-D-arabinofuranosyl)-5-ethynylcytosine.

1-(3-O-acetyl-5-O-benzoyl-2-deoxy-2-fluoro-β-D-arabinofuranosyl)-5-aminocytosine.

1-(3-O-acetyl-5-O-benzoyl-2-deoxy-2-fluoro-β-D-arabinofuranosyl)-5-benzylaminocytosine.

1-(3-O-acetyl-5-O-benzoyl-2-deoxy-2-fluoro-β-D-arabinofuranosyl)-5-aminomethylcytosine.

1-(3-O-acetyl-5-O-benzoyl-2-deoxy-2-fluoro-β-D-arabinofuranosyl)-5-hydroxymethylcytosine.

1-(3-O-acetyl-5-O-benzoyl-2-deoxy-2-fluoro-β-D-arabinofuranosyl)-6-azacytosine.

1-(3-O-acetyl-5-O-benzoyl-2-deoxy-2-fluoro-β-D-arabinofuranosyl)-5-methyl-6-azacytosine.

By following the same procedure but using 3,5-di-O-acetyl-2-chloro-2-deoxy-α-D-arabinofuranosyl bromide and the corresponding cytosine analogs as starting materials, the following nucleosides are prepared:

1-(3,5-di-O-acetyl-2-chloro-2-deoxy-β-D-arabinofuranosyl)-5-fluorocytosine.

1-(3,5-di-O-acetyl-2-chloro-2-deoxy-β-D-arabinofuranosyl)-5-chlorocytosine.

1-(3,5-di-O-acetyl-2-chloro-2-deoxy-β-D-arabinofuranosyl)-5-bromocytosine.

1-(3,5-di-O-acetyl-2-chloro-2-deoxy-β-D-arabinofuranosyl)-5-iodocytosine.

1-(3,5-di-O-acetyl-2-chloro-2-deoxy-β-D-arabinofuranosyl)-5-methylcytosine.

1-(3,5-di-O-acetyl-2-chloro-2-deoxy-β-D-arabinofuranosyl)-5-methyl-6-azacytosine.

By following the same procedure but using 3,5-di-O-acetyl-2-bromo-2-deoxy-α-D-arabinofuranosyl bromide and the corresponding cytosine analogs as starting materials, the following compounds are obtained:

1-(3,5-di-O-acetyl-2-bromo-2-deoxy-β-D-arabinofuranosyl)cytosine.

1-(3,5-di-O-acetyl-2-bromo-2-deoxy-β-D-arabinofuranosyl)-5-fluorocytosine.

1-(3,5-di-O-acetyl-2-bromo-2-deoxy-β-D-arabinofuranosyl)-5-chlorocytosine.

1-(3,5-di-O-acetyl-2-bromo-2-deoxy-β-D-arabinofuranosyl)-5-bromocytosine.

1-(3,5-di-O-acetyl-2-bromo-2-deoxy-β-D-arabinofuranosyl)-5-iodocytosine.

1-(3,5-di-O-acetyl-2-bromo-2-deoxy-β-D-arabinofuranosyl)-5-methylcytosine.

1-(3,5-di-O-acetyl-2-bromo-2-deoxy-β-D-arabinofuranosyl)-5-methyl-6-azacytosine.

EXAMPLE 2

A mixture of 3-O-acetyl-5-O-benzoyl-2-deoxy-2-fluoro-D-arabinofuranosyl bromide (11.5 g) and 2,4-bis(trimethylsilyloxy)pyrimidine [prepared by refluxing a mixture of 5 g of uracil and 5–15 mg of ammonium sulfate in 25 ml of hexa-methyldisilazane until a clear solution is obtained followed by removal of the excess hexamethyldisilazane in vacuo] in 150 ml of methylene chloride is stirred for 5 days at room temperature. Methanol (5 ml) is added to the mixture and the suspension is filtered through a celite pad. The filtrate is evaporated in vacuo and the residue is triturated with diethyl ether to give a crude product which was recrystallized from ethanol to give pure 1-(3-O-acetyl-5-O-benzoyl-2-deoxy-2-fluoro-β-D-arabinofuranosyl)uracil, 5.8 g, m.p. 179°–180°.

Microanalysis ($C_{18}H_{17}F N_2O_7$). Calcd. C, 55.10, H, 4.37; F, 4.84; N, 7.14. Found: C, 54.93; H, 4.42; F, 4.78; N, 7.04.

By following the same procedure but using the corresponding uracil analogs as starting materials, the following compounds are also prepared:

1-(3-O-acetyl-5-O-benzoyl-2-deoxy-2-fluoro-β-D-arabinofuranosyl)-5-fluorouracil.
1-(3-O-acetyl-5-O-benzoyl-2-deoxy-2-fluoro-β-D-arabinofuranosyl)-5-chlorouracil.
1-(3-O-acetyl-5-O-benzoyl-2-deoxy-2-fluoro-β-D-arabinofuranosyl)-5-bromouracil.
1-(3-O-acetyl-5-O-benzoyl-2-deoxy-2-fluoro-β-D-arabinofuranosyl)-5-iodouracil.
1-(3-O-acetyl-5-O-benzoyl-2-deoxy-2-fluoro-β-D-arabinofuranosyl)-4-S-methylthiouracil.
1-(3-O-acetyl-5-O-benzoyl-2-deoxy-2-fluoro-β-D-arabinofuranosyl)-6-azathymine.

In accordance with the above procedure, but where in place of 3-O-acetyl-5-O-benzoyl-2-deoxy-2-fluoro-D-arabinofuranosyl bromide there is used 3,5-di-O-acetyl-2-chloro-2-deoxy-α-D-arabinofuranosyl chloride, there are obtained the following compounds:
1-(3,5-di-O-acetyl-2-chloro-2-deoxy-β-D-arabinofuranosyl)-5-fluorouracil.
1-(3,5-di-O-acetyl-2-chloro-2-deoxy-β-D-arabinofuranosyl)-5-chlorouracil.
1-(3,5-di-O-acetyl-2-chloro-2-deoxy-β-D-arabinofuranosyl)-5-bromouracil.
1-(3,5-di-O-acetyl-2-chloro-2-deoxy-β-D-arabinofuranosyl)-5-iodouracil.
1-(3,5-di-O-acetyl-2-chloro-2-deoxy-β-D-arabinofuranosyl)-thymine.
1-(3,5-di-O-acetyl-2-chloro-2-deoxy-β-D-arabinofuranosyl)-6-azathymine.

In accordance with the principal example above, but using 3,5-di-O-acetyl-2-bromo-2-deoxy-D-arabinofuranosyl bromide in place of 3-O-acetyl-5-O-benzoyl-2-deoxy-2-fluoro-D-arabinofuranosyl bromide, there are obtained the following compounds:
1-(3,5-di-O-acetyl-2-bromo-2-deoxy-β-D-arabinofuranosyl)-5-fluorouracil.
1-(3,5-di-O-acetyl-2-bromo-2-deoxy-β-D-arabinofuranosyl)-5-chlorouracil.
1-(3,5-di-O-acetyl-2-bromo-2-deoxy-β-D-arabinofuranosyl)-5-bromouracil.
1-(3,5-di-O-acetyl-2-bromo-2-deoxy-β-D-arabinofuranosyl)-5-iodouracil.
1-(3,5-di-O-acetyl-2-bromo-2-deoxy-β-D-arabinofuranosyl)-thymine.
1-(3,5-di-O-acetyl-2-bromo-2-deoxy-β-D-arabinofuranosyl)-6-azathymine.

EXAMPLE 3

A mixture of 1-(3-O-acetyl-5-O-benzoyl-2-deoxy-2-fluoro-β-D-arabinofuranosyl)-5-fluorocytosine (650 mg) in 80% acetic acid (50 ml) is heated under reflux for 48 hours. After removal of the solvent in vacuo the residue is chromatographed over a column of silica gel G60 (22×2 cm) using $CHCl_3$:MeOH (30:1 v/v) as the eluent. Each fraction is checked by tlc and the appropriate fractions are collected and evaporated in vacuo, and the residue is crystallized from ethanol to give pure 1-(3-O-acetyl-5-O-benzoyl-2-deoxy-2-fluoro-β-D-arabinofuranosyl)-5-fluorouracil, 300 mg, m.p. 177°–179°.

Analysis ($C_{18}H_{16}F_2N_2O_7$). Calcd. C, 52.69; H, 3.93; F, 9.26; N, 6.83. Found: C, 52.68; H, 3.90; F, 9.60; N, 6.92.

By following the same procedure the following uracil nucleosides are prepared from the corresponding cytosine nucleosides:
1-(3-O-acetyl-5-O-benzoyl-2-deoxy-2-fluoro-β-D-arabinofuranosyl)-5-chlorouracil.
1-(3-O-acetyl-5-O-benzoyl-2-deoxy-2-fluoro-β-D-arabinofuranosyl)-5-bromouracil.
1-(3-O-acetyl-5-O-benzoyl-2-deoxy-2-fluoro-β-D-arabinofuranosyl)-5-iodouracil.
1-(3-O-acetyl-5-O-benzoyl-2-deoxy-2-fluoro-β-D-arabinofuranosyl)-6-azauracil.
1-(3-O-acetyl-5-O-benzoyl-2-deoxy-2-fluoro-β-D-arabinofuranosyl)-6-azathymine.

EXAMPLE 4

1-(3-O-Acetyl-5-O-benzoyl-2-deoxy-2-fluoro-β-D-arabinofuranosyl)-5-bromocytosine (1.0 g) is dissolved in saturated methanolic ammonia (100 ml) and the solution is left standing for 24 hours at room temperature. The solvent is removed in vacuo and the residue was crystallized from ethanol to give 560 mg of 1-(2-deoxy-2-fluoro-β-D-arabinofuranosyl)-5-bromocytosine, m.p. 201°–202°.

Analysis ($C_9H_{11}BrFN_3O_4$). Calcd. C, 33.55; H, 3.42; F, 5.86; N, 12.97. Found: C, 33.30; H, 3.70; F, 5.68; N, 12.69.

By following the same procedure, the following compounds are prepared from the corresponding blocked nucleosides listed in Example 1:
1-(2-deoxy-2-fluoro-β-D-arabinofuranosyl)-5-chlorocytosine.
1-(2-deoxy-2-fluoro-β-D-arabinofuranosyl)-5-iodocytosine.
1-(2-deoxy-2-fluoro-β-D-arabinofuranosyl)-5-methylcytosine.
1-(2-deoxy-2-fluoro-β-D-arabinofuranosyl)-5-ethylcytosine.
1-(2-deoxy-2-fluoro-β-D-arabinofuranosyl)-5-benzylcytosine.
1-(2-deoxy-2-fluoro-β-D-arabinofuranosyl)-5-phenylcytosine.
1-(2-deoxy-2-fluoro-β-D-arabinofuranosyl)-5-vinylcytosine.
1-(2-deoxy-2-fluoro-β-D-arabinofuranosyl)-5-ethynylcytosine.
1-(2-deoxy-2-fluoro-β-D-arabinofuranosyl)-5-aminocytosine.
1-(2-deoxy-2-fluoro-β-D-arabinofuranosyl)-5-benzylaminocytosine.
1-(2-deoxy-2-fluoro-β-D-arabinofuranosyl)-5-aminomethylcytosine.
1-(2-deoxy-2-fluoro-β-D-arabinofuranosyl)-5-hydroxymethylcytosine.
1-(2-deoxy-2-fluoro-β-D-arabinofuranosyl)-5-methyl-6-azacytosine.
1-(2-deoxy-2-fluoro-β-D-arabinofuranosyl)-5-fluorocytosine.

By following the same procedure but using saturated methanolic HCl in place of methanolic $NH_3$ with the corresponding blocked nucleosides, the following compounds are prepared:
1-(2-chloro-2-deoxy-β-D-arabinofuranosyl)-5-fluorocytosine hydrochloride.
1-(2-chloro-2-deoxy-β-D-arabinofuranosyl)-5-chlorocytosine hydrochloride.
1-(2-chloro-2-deoxy-β-D-arabinofuranosyl)-5-bromocytosine hydrochloride.
1-(2-chloro-2-deoxy-β-D-arabinofuranosyl)-5-iodocytosine hydrochloride.
1-(2-chloro-2-deoxy-β-D-arabinofuranosyl)-5-methylcytosine hydrochloride.
1-(2-chloro-2-deoxy-β-D-arabinofuranosyl)-5-methyl-6-azacytosine hydrochloride.

1-(2-bromo-2-deoxy-β-D-arabinofuranosyl)-5-fluorocytosine hydrochloride.

1-(2-bromo-2-deoxy-β-D-arabinofuranosyl)-5-chlorocytosine hydrochloride.

1-(2-bromo-2-deoxy-β-D-arabinofuranosyl)-5-bromocytosine hydrochloride.

1-(2-bromo-2-deoxy-β-D-arabinofuranosyl)-5-iodocytosine hydrochloride.

1-(2-bromo-2-deoxy-β-D-arabinofuranosyl)-5-methylcytosine hydrochloride.

1-(2-bromo-2-deoxy-β-D-arabinofuranosyl)-5-methyl-6-azacytosine hydrochloride.

EXAMPLE 5

1-(3-O-Acetyl-5-O-benzoyl-2-deoxy-2-fluoro-β-D-arabinofuranosyl)thymine (150 mg) is dissolved in saturated methanolic ammonia (15 ml), and the mixture left standing for 16 hours. The solvent is removed by evaporation in vacuo, and the residue crystallized from water to give 80 mg of 1-(2-deoxy-2-fluoro-β-D-arabinofuranosyl)thymine, m.p. 185°–185.5°.

Microanalysis ($C_{10}H_{13}FN_2O_5$). Calcd. C, 46.15; H, 5.00; F, 7.30; N, 10.76. Found: C, 45.98; H, 4.89; F, 7.16; N, 10.58.

By following the same procedure but using the corresponding blocked nucleosides the following compounds are prepared:

1-(2-deoxy-2-fluoro-β-D-arabinofuranosyl)-5-fluorouracil.

1-(2-deoxy-2-fluoro-β-D-arabinofuranosyl)-5-chlorouracil.

1-(2-deoxy-2-fluoro-β-D-arabinofuranosyl)-5-bromouracil.

1-(2-deoxy-2-fluoro-β-D-arabinofuranosyl)-5-iodouracil.

1-(2-deoxy-2-fluoro-β-D-arabinofuranosyl)-6-azathymine.

In accordance with the principal example above, but using saturated methanolic hydrogen chloride in place of methanolic ammonia with the corresponding di-O-acetyl nucleosides, there are obtained the following compounds:

1-(2-chloro-2-deoxy-β-D-arabinofuranosyl)-5-fluorouracil.

1-(2-chloro-2-deoxy-β-D-arabinofuranosyl)-5-chlorouracil.

1-(2-chloro-2-deoxy-β-D-arabinofuranosyl)-5-bromouracil.

1-(2-chloro-2-deoxy-β-D-arabinofuranosyl)-5-iodouracil.

1-(2-chloro-2-deoxy-β-D-arabinofuranosyl)thymine.

1-(2-chloro-2-deoxy-β-D-arabinofuranosyl)-6-azathymine.

1-(2-bromo-2-deoxy-β-D-arabinofuranosyl)-5-fluorouracil.

1-(2-bromo-2-deoxy-β-D-arabinofuranosyl)-5-chlorouracil.

1-(2-bromo-2-deoxy-β-D-arabinofuranosyl)-5-bromouracil.

1-(2-bromo-2-deoxy-β-D-arabinofuranosyl)-5-iodouracil.

1-(2-bromo-2-deoxy-β-D-arabinofuranosyl)thymine.

1-(2-bromo-2-deoxy-β-D-arabinofuranosyl)-6-azathymine.

EXAMPLE 6

To a solution of 1-(3-O-acetyl-5-O-benzoyl-2-deoxy-2-fluoro-β-D-arabinofuranosyl)uracil (500 mg) and sodium acetate (100 mg) in 5 ml of glacial acetic acid is added a solution of bromine (240 mg) in 1 ml of glacial acetic acid. After 30 minutes at room temperature, the solvent is removed by evaporation in vacuo. Traces of acetic acid is removed by several co-evaporation with toluene. The residue is dissolved in saturated methanolic ammonia (50 ml) and the mixture is kept standing at room temperature for 2 days. The solvent is removed by evaporation in vacuo and the residue is crystallized from water to give 1-(2-deoxy-2-fluoro-β-D-arabinofuranosyl)-5-bromouracil (325 mg), m.p. 214°–216°.

Analysis ($C_9H_{10}BrFN_2O_5$). Calcd. C, 33.25; H, 3.10; F, 5.85; N, 8.62. Found: C, 33.57; H, 3.30; F, 5.89; N, 8.66.

In accordance with the above procedure, but where 1-(3,5-di-O-acetyl-2-chloro-2-deoxy-β-D-arabinofuranosyl)uracil or 1-(3,5-di-O-acetyl-2-bromo-2-deoxy-β-D-arabinofuranosyl)uracil is sued in place of 1-(3O-acetyl-5-O-benzoyl-2-deoxy-2-fluoro-β-D-arabinofuranosyl)uracil and where methanol hydrogen chloride is used in place of methanolic ammonia, there is obtained 1-(2-chloro-2-deoxy-β-D-arabinofuranosyl)-5-bromouracil and 1-(2-bromo-2-deoxy-β-D-arabinofuranosyl)-5-bromouracil. All these 5-bromouracil nucleosides obtained in Example 6 are identical in all respects with the corresponding nucleosides prepared as described in Example 5.

EXAMPLE 7

To a mixture of 1-(3-O-acetyl-5-O-benzoyl-2-deoxy-2-fluoro-β-D-arabinofuranosyl)uracil (400 mg) and iodine (130 mg) in glacial acetic acid (5 ml) is added fuming nitric acid (sp. gr. 1.5) dropwise with stirring until the color of iodine disappears. After evaporation in vacuo, the residue is triturated with water and the insoluble product (515 mg) is collected by filtration.

The crude product (200 mg) is dissolved in saturated methanolic ammonia (50 ml). After 2 days, the solvent is removed by evaporation and the residue dissolved in a small amount of ethanol. To the solution is added diethyl ether and the product is collected by filtration and recrystallized from ethanol to give 86 mg of 1-(2-deoxy-2-fluoro-β-D-arabinofuranosyl)-5-iodouracil, m.p. 216°–217°.

Microanalysis ($C_9H_{10}FIN_2O_5$). Calcd. C, 29.05; H, 2.71; F, 5.11; N, 7.53. Found: C, 29.11; H, 2.87; F, 4.99; N, 7.50.

In accordance with the above procedure but where, in place of 1-(3-O-acetyl-5-O-benzoyl-2-deoxy-2-fluoro-β-D-arabinofuranosyl)uracil and methanolic ammonia, there is used a combination of 1-(3,5-di-O-acetyl-2-chloro-2-deoxy-β-D-arabinofuranosyl)uracil or 1-(3,5-di-O-acetyl-2-bromo-2-deoxy-β-D-arabinofuranosyl)uracil and methanolic hydrogen chloride, there are obtained 1-(2-chloro-2-deoxy-β-D-arabino-furanosyl)-5-iodouracil and 1-(2-bromo-2-deoxy-β-D-arabinofuranosyl)-5-iodouracil. All the 5-iodouracil nucleosides obtained in this Example are identical in all respects with the corresponding compounds prepared as described in Example 5.

EXAMPLE 8

A mixture of 1-(2-deoxy-2-fluoro-β-D-arabinofuranosyl)cytosine hydrochloride (610 mg), glacial acetic acid (2.2 ml), iodic acid (196 mg), iodine (327 mg), carbon tetrachloride (1.5 ml) and water (0.75 ml) is stirred at 40°–50° C. for 2.5 hours then at room temperature overnight. Water (6 ml) is added and yellow precipitates [650 mg, m.p. 115°–125° (dec)] filtered, dissolved in 100 ml of water, and the red-brown solution is passed through a column of Amberlite 1R-45 (OH⁻, 25 ml). The column is washed with water (200 ml). The combined eluates and washings are evaporated in vacuo and the colorless residue dissolved in methanolic hydrogen chloride (10 ml). 1-(2-Deoxy-2-fluoro-β-D-arabinofuranosyl)-5-iodocytosine hydrochloride (190 mg) deposits as colorless crystals, m.p. 177°–181° (dec).

Analysis. ($C_9H_{11}FIN_3O_4HCl$). Calcd. C, 26.50; H, 2.94; F, 4.66; N, 10.30. Found: C, 26.55; H, 3.06; F, 4.44; N, 10.20.

In accordance with the above procedure, but where in place of 1-(2-deoxy-2-fluoro-β-D-arabinofuranosyl)-cytosine there is used 1-(2-chloro-2-deoxy-β-D-arabinofuranosyl)cytosine or 1-(2-bromo-2-deoxy-β-D-arabinofuranosyl)cytosine, there are obtained 1-(2-chloro-2-deoxy-β-D-arabinofuranosyl)-5-iodocytosine hydrochloride and 1-(2-bromo-2-deoxy-β-D-arabinofuranosyl)-5-iodocytosine hydrochloride. All these 5-iodocytosine nucleosides obtained in this Example are identical in all respects with the corresponding compounds prepared as described in Example 4.

BIOLOGICAL ACTIVITY

Compounds of the invention show anti-viral and anti-tumor activity. 1-(2-Deoxy-2-fluoro-β-D-arabinofuranosyl)-5-iodocytosine inhibits Herpes Simplex Virus type 1 and type 2 replication. HFEM, Patton, 2931, and F-strain HSV-1 and 333 and G-strain HSV-2 are affected at concentrations of 1-(2-deoxy-2-fluoro-β-D-arabinofuranosyl)-5-iodocytosine 0.01 μM (approximately 0.004 μg/ml).

Studies with a thymidine kinase negative strain of HSV-1 (HSV-1 TK⁻) was found not to be affected by 1-(2-deoxy-2-fluoro-β-D-arabinofuranosyl)-5-iodocytosine at concentrations of up to 10 μM indicating that selectivity probably depends on viral thymidine kinase phosphorylation of 1-(2-deoxy-2-fluoro-β-D-arabinofuranosyl)-5-iodocytosine.

Studies with cytomegalovirus (CMV strain AD 169) have demonstrated 1-(2-deoxy-2-fluoro-β-D-arabinofuranosyl)-5-iodocytosine activity against this other herpes-virus. This is surprising since CMV does not have its own thymidine kinase and must induce a cellular fetal enzyme for replication. At concentrations of 1 μM (0.4 μg/ml), 1-(2-deoxy-2-fluoro-β-D-arabinofuranosyl)-5-iodocytosine was found to reduce CMV plaque formation on WI-38 cells.

The effective doses for 1-(2-deoxy-2-fluoro-β-D-arabinofuranosyl)-5-iodocytosine are given below. 1-(2-deoxy-2-fluoro-β-D-arabinofuranosyl)-5-iodocytosine is diluted in physiological saline, filter sterilized, and inoculated. This compound is readily soluble at concentrations of 25 mg/ml in saline. In mouse studies, the drug is inoculated by the intraperitoneal route.

| Herpes Simplex Virus - type 1 | $ED_{50}$ |
|---|---|
| 1. Strain 2931 | .007 μM |
| 2. Strain McIntyre | * <.01 μM |
| 3. Strain Patton | .01 μM |
| 4. Strain HFEM | * < <.01 μM |
| Herpes Simplex Virus - type 2 | |
| 1. Strain G | .01 μM |
| 2. Strain 333 | .05 μM |
| Cytomegalovirus | |
| 1. Strain AD-169 | 1.0 μM |

* < = less than

The capacity of 2'-fluoro-arabinosyl nucleosides (Formulas IV and V shown below) to suppress replication of Herpes Simplex virus-type 1 (HSV-1) in monolayers of Vero cells is shown in Table I.

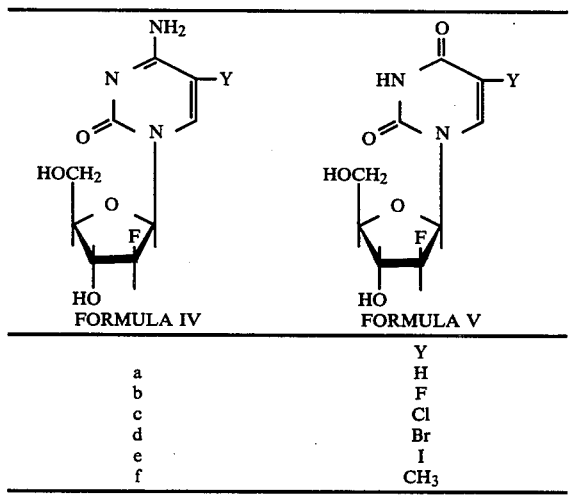

| | Y |
|---|---|
| a | H |
| b | F |
| c | Cl |
| d | Br |
| e | I |
| f | $CH_3$ |

Vero cell monolayers were infected with approximately 1 plaque forming unit (PFU) per cell of Herpes Simplex Virus—Type 1 (HSV-1) strain 2931 and incubated for 2 hr. Maintenance media containing the various concentrations of drugs were used to overlay the monolayers. Supernatant fluids were collected 24 hr. later and titered on Vero cell monolayers described in Lopez et al, Ann. N.Y. Acad. Sci., 284, 351 (1977). Percent inhibition over controls was calculated.

TABLE I

Capacity of 2'-Fluoro-2'-deoxy-arabinosyl-cytosines and -uracils to Suppress HSV-1 Replication in Monolayers of Vero Cells

| Cyto-sine | Nucleo-sides*** | Anti-viral Activity* in μg/ml | | | | | Cytoxicity $ID_{50}$ in μg/ml***** | |
|---|---|---|---|---|---|---|---|---|
| | | 0.01 | 0.1 | 1.0 | 10 | 100 | L51784 | P815 |
| | Y = | | | | | | | |
| IVa** | H | − | + | + | +++ | ++++ | 0.05 | 0.05 |
| IVb | F | − | + | ++ | +++ | ND**** | 0.5 | 0.4 |
| IVc | Cl | − | − | − | +++ | ND | 1.4 | ~1.0 |
| IVd | Br | − | + | ++ | +++++ | ND | ~10 | >10 |
| IVe | I | + | ++++++ | +++++ | +++++ | | 48 | 14 |
| Uracil | Nucleo-sides | | | | | | | |
| Va | H | − | − | ++ | ++ | ND | >10 | >10 |

TABLE I-continued
Capacity of 2'-Fluoro-2'-deoxy-arabinosyl-cytosines and -uracils to Suppress HSV-1 Replication in Monolayers of Vero Cells

|    |    | Anti-viral Activity* in μg/ml | | Cytoxicity ID$_{50}$ in μg/ml***** | |
|----|----|------|------|----|-----|
| Vb | F  | − ++ ++++ | ++++ | ND | 1.0 | 0.7 |
| Vc | Cl | − − − | ++++ | ND | 1.4 | 3.4 |
| Vd | Br | − − ++ | +++ | ND | 0.9 | 1.6 |
| Ve | I  | − + +++ | ++++ | ND | 0.9 | 0.8 |

*% Reduction of HSV-1 titer; >90% = +; >99% = ++; >99.9% = +++; >99.99% = ++++, complete obviation of HSV-1 replication = +++++. (−) = <90% reduction of HSV-1 titer.
**Wright et al, J. Med. Chem., 13, 269 (1970). See also Reichmen et al, Carbohydr. Res., 42, 233 (1975).
***All pyrimidine nucleosides listed in this Table are in the neutral form except for compound IVe which is in the form of its hydrochloride salt.
****ND = not alone
*****Concentration required for 50% inhibition of growth of cells in vitro after 96 hrs. incubation at 37° C.

1-(2-deoxy-2-fluoro-β-D-arabinofuranosyl)-5-iodocytosine was also shown to be active in vivo. A/J mice were inoculated with approximately 50 LD$_{50}$ of HSV-1 strain 2931 intraperitoneally and then treated with 1-(2-deoxy-2-fluoro-β-D-arabinofuranosyl)-5-iodocytosine starting 24 hours later. 1-(2-deoxy-2-fluoro-β-D-arabinofuranosyl)-5-iodocytosine was given at 10 and 1 mg/kg/da for 5 days. Untreated mice died 8 days after inoculation. Five of 10 mice treated with 10 mg/kg/day survived the 21 day experiment. Two of 10 treated with 1 mg/kg/da survival the 21 day experiment and the remainder died an average of 10 days after inoculation. The 1-(2-deoxy-2-fluoro-β-D-arabinofuranosyl)-5-iodocytosine was thus active in vivo against HSV-1.

Since 1-(2-deoxy-2-fluoro-β-D-arabinofuranosyl)-5-iodocytosine was active against a virus which uses fetal thymidine kinase and since many tumor cells express high concentrations of fetal thymidine kinase, it was tested as a selective anti-tumor agent. In vitro the 1-(2-deoxy-2-fluoro-β-D-arabinofuranosyl)-5-iodocytosine was found to suppress the replication of K 562 cells, a cell line of chronic myelogenous leukemia cells, at a concentration of 0.04 μg/ml.

Since 1-(2-deoxy-2-fluoro-β-D-arabinofuranosyl)-5-iodocytosine was not toxic to normal lymphoblastoid cells at concentrations of up to 10 μM, the compound is believed to affect tumor cells at concentrations 1/100th those needed to suppress normal cell replication. Compounds of the invention can be used as a selective treatment for tumors expressing the fetal thymidine kinase which includes most tumors.

The process of treating viral infections and tumors according to this invention comprises administering to a warm-blooded animal having a viral infection and/or an abnormal proporation of leukocytes or other evidences of a malignancy, a therapeutic nontoxic amount of a compound of the invention such as 1-(2-deoxy-2-fluoro-β-D-arabinofuranosyl)-5-iodocytosine, as such or in the form of a pharmaceutically acceptable salt thereof. The invention also provides a pharmaceutical composition in dosage unit form comprising from 10 to about 100 mg/kg of a compound of the invention, per dosage unit, together with a pharmaceutically acceptable nontoxic inert carrier of diluent therefor as described above.

What is claimed is:
1. Pyrimidine nucleosides having the formula

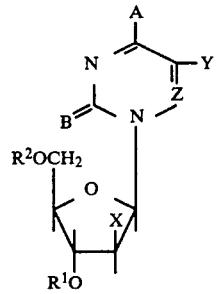

wherein
A is $OR^3$, $SR^3$, $NR^3R^4$ or NHacyl wherein $R^3$ and $R^4$ are the same or different and are hydrogen, lower alkyl of 1 to 7 carbon atoms, aralkyl containing 1 to 20 carbon atoms in the alkyl portion and 6–18 carbon atoms in the aryl portion, or aryl containing 6–18 carbon atoms;
NHacyl is alkanoyl containing 1–20 carbon atoms in the alkyl portion or aroyl amide selected from the group consisting of benzoyl and naphthoyl amide wherein the aromatic group may be substituted by alkyl or alkoxy of 1–20 carbon atoms, halo or nitro;
B is oxygen or sulfur;
X is halogen, alkylsulfonyl containing 1–20 carbon atoms in the alkyl portion or arylsulfonyl containing 6–18 carbon atoms in the aryl portion;
Y is halogen, amino, monoalkyl- containing 1–20 carbon atoms in the alkyl portion or monoaralkylamino containing 1 to 20 carbon atoms in the alkyl portion and 6–18 carbon atoms in the aryl portion, dialkylamino containing 1–20 carbon atoms in the alkyl portion, aminomethyl, hydroxymethyl, lower alkyl, aryl containing 6–18 carbon atoms, aralkyl containing 1 to 20 carbon atoms in the alkyl portion and 6–18 carbon atoms in the aryl portion, vinyl and substituted vinyl or ethynyl and substituted ethynyl;
Z is methyne or nitrogen;
$R^1$ and $R^2$ are the same or different and are hydrogen alkanoyl containing 1–20 carbon atoms in the alkyl portion or aroyl selected from the group consisting of benzoyl and naphthoyl wherein the aromatic group may be substituted by alkyl or alkoxy of 1–20 carbon atoms, halo or nitro.
2. Nucleosides of claim 1 selected from the group of 1-(3-O-acetyl-5-O-benzoyl-2-deoxy-2-fluoro-β-D-arabinofuranosyl)-5-chlorocytosine,
1-(3-O-acetyl-5-O-benzoyl-2-deoxy-2-fluoro-β-D-arabinofuranosyl)-5-bromocytosine, 1-(3-O-acetyl-5-O-benzoyl-2-deoxy-2-fluoro-β-D-arabinofuranosyl)-5-iodocytosine,
1-(3-O-acetyl-5-O-benzoyl-2-deoxy-2-fluoro-β-D-arabinofuranosyl)-5-methylcytosine,
1-(3-O-acetyl-5-O-benzoyl-2-deoxy-2-fluoro-β-D-arabinofuranosyl)-5-ethylcytosine,
1-(3-O-acetyl-5-O-benzoyl-2-deoxy-2-fluoro-β-D-arabinofuranosyl)-5-benzylcytosine,
1-(3-O-acetyl-5-O-benzoyl-2-deoxy-2-fluoro-β-D-arabinofuranosyl)-5-phenylcytosine,
1-(3-O-acetyl-5-O-benzoyl-2-deoxy-2-fluoro-β-D-arabinofuranosyl)-5-vinylcytosine,
1-(3-O-acetyl-5-O-benzoyl-2-deoxy-2-fluoro-β-D-arabinofuranosyl)-5-ethynylcytosine,
1-(3-O-acetyl-5-O-benzoyl-2-deoxy-2-fluoro-β-D-arabinofuranosyl)-5-aminocytosine,
1-(3-O-acetyl-5-O-benzoyl-2-deoxy-2-fluoro-β-D-arabinofuranosyl)-5-benzylaminocytosine,
1-(3-O-acetyl-5-O-benzoyl-2-deoxy-2-fluoro-β-D-arabinofuranosyl)-5-aminomethylcytosine,
1-(3-O-acetyl-5-O-benzoyl-2-deoxy-2-fluoro-β-D-arabinofuranosyl)-5-hydroxymethylcytosine,
1-(3-O-acetyl-5-O-benzoyl-2-deoxy-2-fluoro-β-D-arabinofuranosyl)-5-methyl-6-azacytosine,
1-(3,5-di-O-acetyl-2-chloro-2-deoxy-β-D-arabinofuranosyl)-5-fluorocytosine,
1-(3,5-di-O-acetyl-2-chloro-2-deoxy-β-D-arabinofuranosyl)-5-chlorocytosine,
1-(3,5-di-O-acetyl-2-chloro-2-deoxy-β-D-arabinofuranosyl)-5-bromocytosine,
1-(3,5-di-O-acetyl-2-chloro-2-deoxy-β-D-arabinofuranosyl)-5-iodocytosine,
1-(3,5-di-O-acetyl-2-chloro-2-deoxy-β-D-arabinofuranosyl)-5-methylcytosine,
1-(3,5-di-O-acetyl-2-chloro-2-deoxy-β-D-arabinofuranosyl)-5-methyl-6-azacytosine,
1-(3,5-di-O-acetyl-2-bromo-2-deoxy-β-D-arabinofuranosyl)-5-fluorocytosine,
1-(3,5-di-O-acetyl-2-bromo-2-deoxy-β-D-arabinofuranosyl)-5-chlorocytosine,
1-(3,5-di-O-acetyl-2-bromo-2-deoxy-β-D-arabinofuranosyl)-5-bromocytosine,
1-(3,5-di-O-acetyl-2-bromo-2-deoxy-β-D-arabinofuranosyl)-5-iodocytosine,
1-(3,5-di-O-acetyl-2-bromo-2-deoxy-β-D-arabinofuranosyl)-5-methylcytosine,
1-(3,5-di-O-acetyl-2-bromo-2-deoxy-β-D-arabinofuranosyl)-5-methyl-6-azacytosine.

3. 1-(3-O-acetyl-5-O-benzoyl-2-deoxy-2-fluoro-β-D-arabinofuranosyl)-5-fluorouracil,
1-(3-O-acetyl-5-O-benzoyl-2-deoxy-2-fluoro-β-D-arabinofuranosyl)-5-chlorouracil,
1-(3-O-acetyl-5-O-benzoyl-2-deoxy-2-fluoro-β-D-arabinofuranosyl)-5-bromouracil,
1-(3-O-acetyl-5-O-benzoyl-2-deoxy-2-fluoro-β-D-arabinofuranosyl)-5-iodouracil,
1-(3-O-acetyl-5-O-benzoyl-2-deoxy-2-fluoro-β-D-arabinofuranosyl)-6-azathymine,
1-(3,5-di-O-acetyl-2-chloro-2-deoxy-β-D-arabinofuranosyl)-5-fluorouracil,
1-(3,5-di-O-acetyl-2-chloro-2-deoxy-β-D-arabinofuranosyl)-5-chlorouracil,
1-(3,5-di-O-acetyl-2-chloro-2-deoxy-β-D-arabinofuranosyl)-5-bromouracil,
1-(3,5-di-O-acetyl-2-chloro-2-deoxy-β-D-arabinofuranosyl)-5-iodouracil,
1-(3,5-di-O-acetyl-2-chloro-2-deoxy-β-D-arabinofuranosyl)-thymine,
1-(3,5-di-O-acetyl-2-chloro-2-deoxy-β-D-arabinofuranosyl)-6-azathymine,
1-(3,5-di-O-acetyl-2-bromo-2-deoxy-β-D-arabinofuranosyl)-5-fluorouracil,
1-(3,5-di-O-acetyl-2-bromo-2-deoxy-β-D-arabinofuranosyl)-5-chlorouracil,
1-(3,5-di-O-acetyl-2-bromo-2-deoxy-β-D-arabinofuranosyl)-5-bromouracil,
1-(3,5-di-O-acetyl-2-bromo-2-deoxy-β-D-arabinofuranosyl)-5-iodouracil,
1-(3,5-di-O-acetyl-2-bromo-2-deoxy-β-D-arabinofuranosyl)-thymine,
1-(3,5-di-O-acetyl-2-bromo-2-deoxy-β-D-arabinofuranosyl)-6-azathymine, 4. Nucleosides of claim 1 selected from the group of
1-(2-deoxy-2-fluoro-β-D-arabinofuranosyl)-5-bromocytosine,
1-(2-deoxy-2-fluoro-β-D-arabinofuranosyl)-5-chlorocytosine,
1-(2-deoxy-2-fluoro-β-D-arabinofuranosyl)-5-fluorocytosine,
1-(2-deoxy-2-fluoro-β-D-arabinofuranosyl)-5-iodocytosine and
1-(2-deoxy-2-fluoro-β-D-arabinofuranosyl)-5-methylcytosine.

5. Nucleosides of claim 1 selected from the group of
1-(2-deoxy-2-fluoro-β-D-arabinofuranosyl)-5-ethylcytosine,
1-(2-deoxy-2-fluoro-β-D-arabinofuranosyl)-5-benzylcytosine,
1-(2-deoxy-2-fluoro-β-D-arabinofuranosyl)-5-phenylcytosine,
1-(2-deoxy-2-fluoro-β-D-arabinofuranosyl)-5-vinylcytosine,
1-(2-deoxy-2-fluoro-β-D-arabinofuranosyl)-5-ethynylcytosine,
1-(2-deoxy-2-fluoro-β-D-arabinofuranosyl)-5-aminocytosine,
1-(2-deoxy-2-fluoro-β-D-arabinofuranosyl)-5-benzylaminocytosine,
1-(2-deoxy-2-fluoro-β-D-arabinofuranosyl)-5-aminomethylcytosine,
1-(2-deoxy-2-fluoro-β-D-arabinofuranosyl)-5-hydroxymethylcytosine,
1-(2-deoxy-2-fluoro-β-D-arabinofuranosyl)-5-methyl-6-azacytosine,
1-(2-chloro-2-deoxy-β-D-arabinofuranosyl)-5-fluorocytosine hydrochloride,
1-(2-chloro-2-deoxy-β-D-arabinofuranosyl)-5-chlorocytosine hydrochloride,
1-(2-chloro-2-deoxy-β-D-arabinofuranosyl)-5-bromocytosine hydrochloride,
1-(2-chloro-2-deoxy-β-D-arabinofuranosyl)-5-iodocytosine hydrochloride,
1-(2-chloro-2-deoxy-β-D-arabinofuranosyl)-5-methylcytosine hydrochloride,
1-(2-chloro-2-deoxy-β-D-arabinofuranosyl)-5-methyl-6-azacytosine hydrochloride,
1-(2-bromo-2-deoxy-β-D-arabinofuranosyl)-5-fluorocytosine hydrochloride,
1-(2-bromo-2-deoxy-β-D-arabinofuranosyl)-5-chlorocytosine hydrochloride,
1-(2-bromo-2-deoxy-β-D-arabinofuranosyl)-5-bromocytosine hydrochloride,
1-(2-bromo-2-deoxy-β-D-arabinofuranosyl)-5-iodocytosine hydrochloride,
1-(2-bromo-2-deoxy-β-D-arabinofuranosyl)-5-methylcytosine hydrochloride, and 1-(2-bromo-2-deoxy-β-D-arabinofuranosyl)-5-methyl-6-azacytosine hydrochloride.

6. Nucleosides of claim 1 selected from the group of 1-(2-deoxy-2-fluoro-β-D-arabinofuranosyl)thymine,
1-(2-deoxy-2-fluoro-β-D-arabinofuranosyl)-5-fluorouracil,
1-(2-deoxy-2-fluoro-β-D-arabinofuranosyl)-5-chlorouracil,
1-(2-deoxy-2-fluoro-β-D-arabinofuranosyl)-5-bromouracil and
1-(2-deoxy-2-fluoro-β-D-arabinofuranosyl)-5-iodouracil.

7. Nucleosides of claim 1 selected from the group of 1-(2-deoxy-2-fluoro-β-D-arabinofuranosyl)-6-azathymine,
1-(2-chloro-2-deoxy-β-D-arabinofuranosyl)-5-fluorouracil,
1-(2-chloro-2-deoxy-β-D-arabinofuranosyl)-5-chlorouracil,
1-(2-chloro-2-deoxy-β-D-arabinofuranosyl)-5-bromouracil,
1-(2-chloro-2-deoxy-β-D-arabinofuranosyl)-5-iodouracil,
1-(2-chloro-2-deoxy-β-D-arabinofuranosyl)thymine,
1-(2-chloro-2-deoxy-β-D-arabinofuranosyl)-6-azathymine,
1-(2-bromo-2-deoxy-β-D-arabinofuranosyl)-5-fluorouracil,
1-(2-bromo-2-deoxy-β-D-arabinofuranosyl)-5-chlorouracil,
1-(2-bromo-2-deoxy-β-D-arabinofuranosyl)-5-bromouracil,
1-(2-bromo-2-deoxy-β-D-arabinofuranosyl)-5-iodouracil,
1-(2-bromo-2-deoxy-β-D-arabinofuranosyl)thymine and,
1-(2-bromo-2-deoxy-β-D-arabinofuranosyl)-6-azathymine.

8. Pharmaceutical composition comprising a nucleoside of the formula defined in claim 1 or a pharmaceutically acceptable acid addition salts thereof together with a pharmaceutically acceptable carrier.

9. Method of producing an anti-viral effect in a test animal which comprises administering to said animal an effective amount of a nucleoside of the formula defined in claim 1 or a pharmaceutically acceptable acid addition salt thereof.

10. Method of producing anti-tumor effect in a test animal which comprises administering to said animal an effective amount of a nucleoside of the formula defined in claim 1 or a pharmaceutically acceptable acid addition salt thereof.

* * * * *

UNITED STATES PATENT AND TRADEMARK OFFICE
CERTIFICATE OF CORRECTION

PATENT NO. : 4,211,773
DATED : July 8, 1980
INVENTOR(S) : Carlos Lopez et al

It is certified that error appears in the above-identified patent and that said Letters Patent are hereby corrected as shown below:

```
col. 12, l. 19, "sued" should read -- used ''
col. 12, l. 20, "30" should read -- 3-0 --
col. 15, l. 11, "Reichmen" should read -- Reichman --
col. 15, l. 3, "alone" should read -- done --
col. 17, l. 49 and l. 50, claim 3, should read
         -- 3. Nucleosides of claim 1 selected
            from the group of --
```

Signed and Sealed this

Seventeenth Day of March 1981

[SEAL]

Attest:

RENE D. TEGTMEYER

Attesting Officer

Acting Commissioner of Patents and Trademarks